United States Patent
Biggs

(10) Patent No.: US 8,210,052 B1
(45) Date of Patent: Jul. 3, 2012

(54) METHOD FOR FORECASTING THE FATIGUE DAMAGE OF A SOLID ROCKET MOTOR THROUGH IGNITION

(75) Inventor: Gary Biggs, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 259 days.

(21) Appl. No.: 12/802,450

(22) Filed: May 20, 2010

(51) Int. Cl.
*G01N 3/08* (2006.01)
(52) U.S. Cl. .......................................... 73/826; 73/808
(58) Field of Classification Search ............. 73/760, 73/799, 808, 826
See application file for complete search history.

(56) References Cited

U.S. PATENT DOCUMENTS

| | | | | |
|---|---|---|---|---|
| 4,722,062 A * | 1/1988 | Breitkopf et al. | | 702/43 |
| 5,038,295 A * | 8/1991 | Husband et al. | | 702/34 |
| 6,301,970 B1 * | 10/2001 | Biggs et al. | | 73/804 |
| 7,212,696 B2 * | 5/2007 | Andrews et | | 385/13 |
| 7,387,031 B1 * | 6/2008 | Perrin et al. | | 73/820 |
| 2007/0135987 A1 * | 6/2007 | Coffey et al. | | 701/100 |
| 2007/0295098 A1 | 12/2007 | Balestra | | |
| 2009/0144038 A1 * | 6/2009 | Rassaian et al. | | 703/6 |
| 2010/0332153 A1 * | 12/2010 | Vegter et al. | | 702/42 |
| 2011/0214509 A1 * | 9/2011 | Hochstetter et al. | | 73/834 |

OTHER PUBLICATIONS http://en.wikipedia.org/wiki/Mnte_Carlo_method.
A.H.Lepie, A. Adicoff,Dynamic mechanical behavior of highly filled polymers: Energy Balances and Damage Mar. 8, 2003; California.
http://www3.interscience.wiley.com/journal/104023479/abstract?CRETRY+1&S.

* cited by examiner

*Primary Examiner* — Max Noori
(74) *Attorney, Agent, or Firm* — Fredric J. Zimmerman

(57) ABSTRACT

The invention includes a method for forecasting fatigue damage of a solid rocket motor through ignition, where over the lifetime of the motor it can be exposed to a plurality of stressing events, which may have a broad spectrum of mechanical loads with multiple modes. For instance, a mode may be a change in the thermal contraction or a change in a direct mechanical load. The method expresses all stressing events in terms of a common mode. The thermal contraction is the selected common mode measured in units of stress. The stress is proportionally adjusted according to the conditioning temperature, the stress free temperature, the pressures, and the age. Cumulative damage for the time before and after ignition is determined. Finite element analysis reference points are adjusted for the stressing events.

20 Claims, 12 Drawing Sheets

Table I

| Motor Conditioning Temperature | °F | | | | | |
|---|---|---|---|---|---|---|
| Stress free temperature, °F | | 150 | 102 | 99 | 95 | 95 |
| Motor age, yrs | | 0 | 4 | 9 | 15 | 20 |
| Ignition pressurization $E_{tan}$, lb/in² | 45 | 2180 | 2250 | 2335 | 2442 | 2529 |
| Ignition Pressurization Grain Bore stress, lb/in² | 45 | 37.4 | 38.6 | 40.1 | 41.9 | 43.4 |
| Ignition Pressurization Grain Bore Stress, lb/in² | 55 | 33.4 | 34.5 | 35.8 | 37.4 | 38.7 |
| Thermal Grain Bore Stress, lb/in² | 45 | 49.8 | 29.3 | 29.7 | 28.6 | 29.3 |
| Thermal Grain Bore Stress, lb/in² | 55 | 43.7 | 23.5 | 23.5 | 22.3 | 22.8 |
| Thermal Grain Bore Stress, lb/in² | 77 | 32.6 | 12.1 | 11.4 | 9.7 | 10.0 |
| Relaxation modulus, aging ratio, $E_R/E_{Rref}$ | | 1.00 | 1.08 | 1.16 | 1.21 | 1.24 |

Table I. Pressurization and thermal bore stresses versus motor age and conditioning temperature with reference finite element modeling results.

*Fig. 2*

Table II

| Loading Condition | T, °F | T, °K | $\log a_T$ | $t_1$, min | Log $t_1/a_T$ minutes | Log$(E_r T_s /T)$ lb/in$^2$ | $E_r$, lb/in$^2$ |
|---|---|---|---|---|---|---|---|
| Ignition | 45 | 280 | 0.669 | 0.00917 | -2.71 | 2.97 | 955 |
| Ignition | 55 | 286 | 0.336 | 0.00917 | -2.37 | 2.9 | 831 |
| Cool Down | 45 | 280 | 0.669 | 2160 | 2.67 | 2.22 | 170 |
| Cool Down | 55 | 286 | 0.336 | 2160 | 3.00 | 2,20 | 165 |
| Cool Down | 77 | 298 | -0.311 | 2160 | 3.65 | 2.17 | 160 |

Table II. Relaxation moduli of unaged propellant versus temperature.

*Fig. 3*

Table III

| T, sec | $\sigma_T$ 55 °F Thermal and Pressure Stress lb/in² | $\sigma_T,$ (avg) 55 °F Thermal and Pressure Stress lb/in² |
|---|---|---|
| 0.00 | 43.7 | |
| 0.05 | 46.8 | 45.2 |
| 0.10 | 49.8 | 48.3 |
| 0.15 | 52.8 | 51.3 |
| 0.20 | 55.9 | 54.4 |
| 0.25 | 58.9 | 57.4 |
| 0.30 | 61.9 | 60.4 |
| 0.35 | 65.0 | 63.5 |
| 0.40 | 68.0 | 66.5 |
| 0.45 | 71.0 | 69.5 |
| 0.50 | 74.1 | 72.6 |
| 0.55 | 77.1 | 75.6 |

Table III. Grain circular bore surface ignition pressurization stress history of a new motor conditioned to 55°F.

*Fig. 4*

Table IV

| $t_i$, sec | $\sigma_0$, lb/in² | B | $a_T$ | $\sigma_T$, (avg) lb/in² | Damage Fraction | Cumulative Damage |
|---|---|---|---|---|---|---|
| 0.05 | 244.50 | 5.59 | 2.17 | 45.25 | 3.11E-08 | 3.11E-08 |
| 0.10 | 244.50 | 5.59 | 2.17 | 48.28 | 4.46E-08 | 7.57E-08 |
| 0.15 | 244.50 | 5.59 | 2.17 | 51.32 | 6.27E-08 | 1.38E-07 |
| 0.20 | 244.50 | 5.59 | 2.17 | 54.35 | 8.65E-08 | 2.25E-07 |
| 0.25 | 244.50 | 5.59 | 2.17 | 57.39 | 1.17E-07 | 3.42E-07 |
| 0.30 | 244.50 | 5.59 | 2.17 | 60.42 | 1.56E-07 | 4.98E-07 |
| 0.35 | 244.50 | 5.59 | 2.17 | 63.46 | 2.05E-07 | 7.04E-07 |
| 0.40 | 244.50 | 5.59 | 2.17 | 66.49 | 2.67E-07 | 9.70E-07 |
| 0.45 | 244.50 | 5.59 | 2.17 | 69.53 | 3.42E-07 | 1.31E-06 |
| 0.50 | 244.50 | 5.59 | 2.17 | 72.56 | 4.34E-07 | 1.75E-06 |
| 0.55 | 244.50 | 5.59 | 2.17 | 75.60 | 5.45E-07 | 2.29E-06 |

Table IV. Bore surface cumulative damage using fatigue parameters from tensile testing under superimposed pressure.

*Fig. 5*

Table V

| $t_i$, sec | $\sigma_0$ lb/in² | B | $a_T$ | $\sigma_T$, (avg) lb/in² | Damage Fraction | Cumulative Damage |
|---|---|---|---|---|---|---|
| 0.05 | 155.50 | 11.07 | 2.17 | 45.25 | 4.48E-10 | 4.48E-10 |
| 0.10 | 164.40 | 10.52 | 2.17 | 48.28 | 9.71E-10 | 1.42E-09 |
| 0.15 | 173.30 | 9.97 | 2.17 | 51.32 | 2.06E-09 | 3.48E-09 |
| 0.20 | 182.20 | 9.42 | 2.17 | 54.35 | 4.31E-09 | 7.80E-09 |
| 0.25 | 191.10 | 8.88 | 2.17 | 57.39 | 8.88E-09 | 1.67E-08 |
| 0.30 | 200.00 | 8.33 | 2.17 | 60.42 | 1.80E-08 | 3.47E-08 |
| 0.35 | 208.90 | 7.78 | 2.17 | 63.46 | 3.63E-08 | 7.10E-08 |
| 0.40 | 217.80 | 7.23 | 2.17 | 66.49 | 7.23E-08 | 1.43E-07 |
| 0.45 | 226.70 | 6.68 | 2.17 | 69.53 | 1.43E-07 | 2.86E-07 |
| 0.50 | 235.60 | 6.13 | 2.17 | 72.56 | 2.80E-07 | 5.66E-07 |
| 0.55 | 244.50 | 5.59 | 2.17 | 75.60 | 5.46E-07 | 1.11E-06 |

Table V. Bore surface cumulative damage using dynamic fatigue parameters.

*Fig. 6*

Table VI

| Total Time days | Mean °F | $\sigma_0$, lb/in² | B | Bore Stress $\sigma_T$, (avg) lb/in² | Damage Fraction | Cumulative Fraction |
|---|---|---|---|---|---|---|
| 2 | 77.0 | 147 | 11.6 | 4.9 | 3.89E-14 | 3.89E-14 |
| 4 | 55.4 | 147 | 11.6 | 6.5 | 2.54E-13 | 2.93E-13 |
| 6 | 33.8 | 147 | 11.6 | 8.5 | 1.12E-12 | 1.41E-12 |
| 8 | 12.2 | 147 | 11.6 | 11.5 | 4.90E-12 | 6.31E-12 |
| 10 | -9.4 | 147 | 11.6 | 16.3 | 2.97E-11 | 3.60E-11 |
| 12 | -31.0 | 147 | 11.6 | 24.9 | 3.39E-10 | 3.75E-10 |
| 14 | -52.6 | 147 | 11.6 | 42.3 | 9.91E-09 | 1.03E-08 |
| 16 | -53.5 | 147 | 11.6 | 43.4 | 1.17E-08 | 2.20E-08 |
| 18 | -54.4 | 147 | 11.6 | 44.5 | 1.39E-08 | 3.59E-08 |
| 20 | -55.3 | 147 | 11.6 | 45.6 | 1.65E-08 | 5.24E-08 |
| 22 | -56.2 | 147 | 11.6 | 46.8 | 1.96E-08 | 7.20E-08 |
| 24 | -57.1 | 147 | 11.6 | 48.0 | 2.34E-08 | 9.53E-08 |
| 26 | -58.0 | 147 | 11.6 | 49.3 | 2.80E-08 | 1.23E-07 |
| 28 | -58.9 | 147 | 11.6 | 50.6 | 3.35E-08 | 1.57E-07 |
| 30 | -59.8 | 147 | 11.6 | 51.9 | 4.02E-08 | 1.97E-07 |
| 32 | -60.7 | 147 | 11.6 | 53.3 | 4.84E-08 | 2.45E-07 |
| 34 | -61.6 | 147 | 11.6 | 54.8 | 5.85E-08 | 3.04E-07 |
| 36 | -62.5 | 147 | 11.6 | 56.3 | 7.07E-08 | 3.75E-07 |
| 38 | -63.4 | 147 | 11.6 | 57.9 | 8.58E-08 | 4.60E-07 |
| 40 | -64.3 | 147 | 11.6 | 59.5 | 1.04E-07 | 5.65E-07 |
| 42 | -65.2 | 147 | 11.6 | 61.2 | 1.27E-07 | 6.92E-07 |
| 44 | -66.1 | 147 | 11.6 | 62.9 | 1.55E-07 | 8.47E-07 |
| 46 | -67.0 | 147 | 11.6 | 64.8 | 1.90E-07 | 1.04E-06 |
| 48 | -67.9 | 147 | 11.6 | 66.7 | 2.34E-07 | 1.27E-06 |
| 50 | -68.8 | 147 | 11.6 | 68.6 | 2.88E-07 | 1.56E-06 |

*Fig. 7*

Fig. 8 illustrates a complex thermal sequence followed by motor ignition.

Fig. 9 illustrates a solid propellant relaxation modulus, $E_r$, versus reduced time $t_1/a_T$ "master curve".

Fig. 10 illustrates the solid propellant temperature sift factor versus temperature.

Fig. 11 illustrates constant strain rate tensile data for a typical solid propellant show that as the strain rate is increased the maximum corrected stress also increases. All specimens were conditioned at ambient temperature prior to testing. Each plotted point is the average of a number of tests.

METHOD FOR FORECASTING THE FATIGUE DAMAGE OF A SOLID ROCKET MOTOR THROUGH IGNITION

STATEMENT OF GOVERNMENT INTEREST

The invention described herein may be manufactured and used by or for the Government of the United States of America for Governmental purposes without the payment of any royalties thereon or therefore.

BACKGROUND OF THE INVENTION

1. Field of the Invention

The invention relates generally to a method of determining the fatigue of structures, and more particularly to a method of forecasting the estimated fatigue damage of a solid propellant rocket motor before and after ignition, based on dynamic and historical parameters including age, thermal contraction, conditioning, pressure, temperature at ignition, and the stress free temperature of the propellant.

2. Background

Grain structural integrity of the solid propellant of rocket motors can be the limiting factor for the usable service life. Structural failure can result in catastrophic motor failure. In the case of solid propellant rocket motors, one of the most common causes for failure is stress arising from thermal contraction. The modeling of stress is complicated as the propellant changes to relieve some of this stress. These changes generally consist of viscous flow of the polymeric binder and changes in crosslinking. As the propellant ages, in general, there is a shift in the stress-free temperature toward a lower temperature.

The level of stress within the motor must be known in order to estimate damage. This level is usually determined by performing a finite element analysis. For complicated structures the corresponding finite element model may be quite large, requiring a significant amount of computation. If the load sequence is long and varied it may be necessary to make many runs of the finite element model to compute the corresponding stress sequence. For moderate to large finite element models, the time needed is often so large that it is not practical to perform the calculation. Rather, engineering judgments and approximations are sometimes made, so that many of the loads suspected of causing little or no damage are ignored. This approach is at best an imprecise process.

U.S. Pat. No. 6,301,970 to Biggs et al. teaches a method of predicting fatigue failure in a filled polymeric material. The method involves the calculation of stress at the region of highest stress using an equation which includes as parameters, regression coefficients of the stress versus modulus obtained from a finite element analysis. Once the regression coefficients are obtained, there is no further need to perform a finite element analysis. The calculated stresses are numerically integrated in a damage equation using a Monte Carlo method. The model provides an estimate of when failure will occur. The Biggs method has been tested in the case of temperature stress loading of a solid propellant rocket motor. The method does not address the effect of ignition, where high pressure and high temperature combustion gases are produced in a very short period of time. Also, the stress model is not specific as to the probable effect on the stress at the bore of the rocket motor.

SUMMARY OF THE INVENTION

The invention includes a method for forecasting the fatigue of a structure, such as a solid rocket motor, where over the lifetime of the structure it may be exposed to a plurality of stressing events which can have a broad spectrum of mechanical loads with multiple modes. For instance, a mode may be a change in thermal contraction or a direct mechanical action under a set of conditions that include an interval of time, temperature, pressure, conditioning, characteristics of the material(s) that make up the structure, and the age of the structure. The invented method for estimating the fatigue expresses all stressing events in terms of a common mode. An aspect of the invention is that thermal contraction, which is measured in units of stress, is the common mode. Another aspect of the invention is that the forecast has an estimate of cumulative damage caused by the spectrum of mechanical loads. Of particular interest is the lifetime of stressing events including the manufacture of the solid rocket motor, the effect of conditioning, the effect of field storage, and the effect of ignition.

An intended application of this method is to forecast ignition fatigue in the propellant in instances where the motor has aged varying amounts and may be conditioned to any arbitrary temperature of interest when ignited. Proportionality is used to adjust reference finite element model results so the references may be applied to any arbitrary combination of motor age and grain conditioning temperature at ignition.

Another aspect of the invention to estimate the stress versus the time histories of interest, computing the cumulative damage of each, identify segment(s) where damage (fatigue) is a maximum, describe a worst case load for the structure, and include dynamic changes in material strength and stiffness owing to aging for long duration load histories. Benefits of the invention include that it allows for direct comparison of fatigue damage magnitudes from differing loads, quickly identifying the worst; ranking loads from entirely different modes, (e.g. thermal contraction and direct mechanical (for example, loading (i.e. stress) of a solid propellant through cooling a case bonded grain rocket motor versus ignition pressurization)), using a computational method that expresses the differing loads in common terms (i.e. damage fractions). The method allows loads that do not have their origin in material thermal contraction to be proportionally expressed in terms of an equivalent load that does. For example, a direct mechanical load can be expressed as a thermal contraction producing the same fatigue damage. The proportionality approach of the method facilitates follow on analysis in other models built exclusively around thermal contraction by building a pure load history only in that mode. Another benefit of utilizing the proportionality approach allows one to modify loads/material strength when problem boundary conditions change (chemical aging of material microstructure, variation in load, etc.). It reduces the need for multiple application of more time intensive analysis, e.g. finite element analysis, and includes independent estimate of load components in instances of mixed loading, e.g. combined thermal and pressurization. As will be seen, the proportionality approach of the method highlights the use of "aging functions." The "aging functions" pick up chemical change of material microstructure, viscoelastic material stress relieving flow phenomenon, and accounts for strength modifying phenomena external to the structure, such as, the improvement often observed when composite propellants are loaded in an environment of superimposed pressure, for instance a solid propellant in an operating rocket motor.

BRIEF DESCRIPTION OF THE DRAWINGS

The foregoing invention will become readily apparent by referring to the following detailed description and the appended drawings in which:

FIG. 2 is Table I, containing data illustrating both ignition pressure grain stress and thermal grain stress versus motor age and conditioning temperature adjusted from reference finite element modeling results;

FIG. 3 is Table II, which contains data illustrating the relationship of relaxation moduli of unaged propellant versus temperature;

FIG. 4 is Table III, which contains data illustrating the circular bore surface ignition pressure grain stress history of a new motor conditioned to 55° F.;

FIG. 5 is Table IV, which contains data illustrating the bore surface cumulative damage using fatigue parameters from tensile testing under superimposed pressure;

FIG. 6 is Table V, which contains data illustrating the bore surface cumulative damage using dynamic fatigue parameters;

FIG. 7 is Table VI, which contains data illustrating that step cooling using modeling based on stress arising from thermal contraction suggests that the ignition pressurization damage produces the same magnitude of cumulative damage as the stress arising from thermal contraction;

DETAILED DESCRIPTION OF THE INVENTION

The propellant in solid rocket motors fatigues as it ages in a large part because the motor case restricts contraction of the solid propellant bonded within it. Generally, a motor case is a pressure chamber having a diameter that is substantially fixed because contraction produces compression of the material forming the case. In addition, the motor case is made of materials that generally have a relatively low thermal expansion in comparison to the propellant. The motor case is generally composed of steel, while the propellant is a filled thermo-viscoelastic polymeric material that is loaded hot (i.e. as a hot viscous material), generally, with a cross-linking agent, cured in an oven and conditioned at ambient temperature when cure is complete. The binder of the propellant is selected, in part, to adhere to the interior walls of the motor case, which can be pre-treated to ensure that the bond between the propellant and the case is excellent. As the propellant cools there is grain thermal contraction, producing thermal grain stress. The thermal grain bore stress $\sigma_T$ is measured in force per area (lbs/in$^2$).

Figure 1:
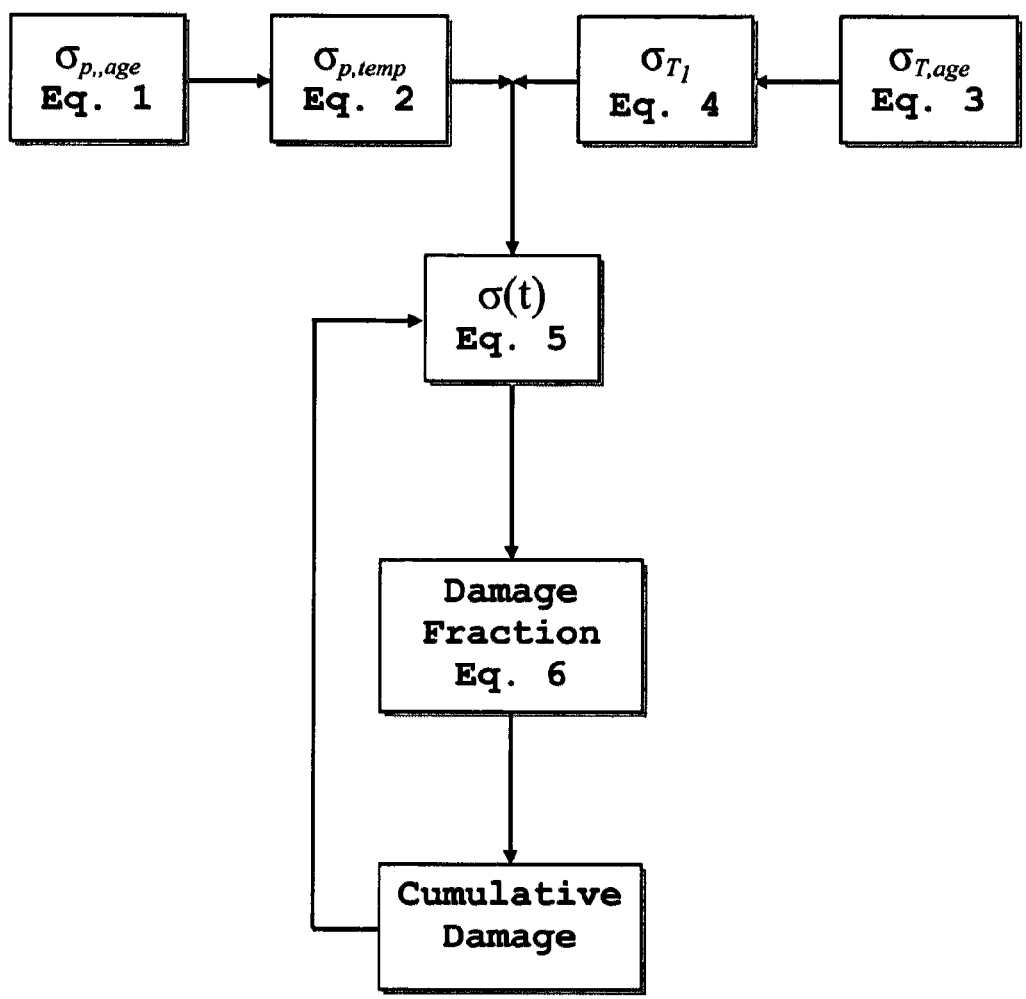
FIG. 1 is a flow diagram that is an overview of the method for estimating the fatigue of a structure over the lifetime of the structure, where the structure is a rocket motor and the lifetime includes ignition.

A flow diagram, that is, an overview of the method for estimating the fatigue of a structure over the lifetime of the structure is illustrated in FIG. 1. The structure (i.e. solid propellant rocket motor) is exposed to a plurality of stressing events, which may have a broad spectrum of mechanical loads with multiple modes. A significant stressing event, measured in units of stress at the bore, is due to ignition, and the stress is proportionally adjusted for the pressure, age and conditioning temperature. Ultimately, the stress to failure in unit time and actual stress are compared with the actual load time to determine the fatigue, which is expressed as a unit-less quantity termed the damage fraction.

The method for forecasting fatigue damage of a solid rocket motor through ignition, includes dissecting a solid propellant rocket motor to obtain grain sections; machining tensile coupons from the grain sections where the tensile coupons are oriented in a direction of maximum stress; performing constant strain rate to failure uni-axial tensile tests with propellant coupons, where the tests are performed at ambient atmospheric pressure for analysis of motor pre-ignition loading and with superimposed pressure for analysis of rocket motor ignition; reducing constant strain rate propellant tensile data to a form that represents constant stress and obtaining a relationship between constant stress and time to failure; obtaining separate relationships for both atmospheric and superimposed motor ignition pressures; performing relaxation modulus testing of propellant coupons; reducing relaxation modulus test results to obtain a master curve of modulus versus reduced time, i.e. $t/a_T$, where t is loading time and $a_T$ is the temperature shift factor; performing bi-rate uni-axial testing of propellant tensile coupons where the first phase test stage simulates slow straining to pre-motor ignition grain thermal contraction strain and the second stage consists of rapid straining with super-imposed pressure to simulate motor ignition, where maximum tangent modulus is measured from stage two and is used to estimate grain ignition stress; performing long term constant strain testing of solid propellant tensile coupons and measuring permanent set over time; reducing observations of permanent set to obtain solid propellant grain stress free temperature over time; accelerating testing of solid propellant grain sections where samples of material are placed in high temperature ovens, each maintained at a different temperature; repeating constant strain rate, relaxation modulus, permanent set, and bi-rate tensile tests upon periodic withdrawal of material from the acceleration temperatures; fitting data to an Arrhenius model for determine the rates at which the individual properties change over time at ambient temperature, where the rates are used to estimate physical and mechanical properties to calculate fatigue damage for ignition of a rocket motor of any arbitrary age of interest; building a finite element analysis reference that comprises a grain stress from pressurization, a relaxation modulus, a tangent modulus, a conditioning temperature, a thermal stress from contraction after manufacture, and a stress free temperature;

adjusting an ignition pressure grain stress at ignition to account for any changes in propellant stiffness from a reference grain stress as indicated by a change from a reference tangent modulus; adjusting the ignition pressure grain stress to account for a difference in an ignition conditioning temperature and a reference conditioning temperature, and a difference in an ignition relaxation modulus and a reference relaxation modulus; adjusting the ignition pressure grain stress to account for a temperature sensitivity to pressure; adjusting a thermal grain stress over an interval of time to account for a difference in a stress free temperature at an age and a reference stress free temperature, and a difference in a relaxation modulus at an age and a reference relaxation modulus; adjusting the thermal grain stress to account for a difference in a second conditioning temperature and a (second) stress free temperature, and a first conditioning temperature and a (first) stress free temperature, and a ratio of relaxation moduli at the second conditioning temperature divided by the relaxation moduli at the first conditioning temperature; determining an ignition stress over a short time interval by adding the thermal grain stress to the ignition pressure grain stress, where the ignition pressure grain stress is a fraction of an instantaneous time divided by a total time for the ignition; determining an average ignition stress by taking the average of the ignition stress at the current time interval and the ignition stress at the previous time interval; determining a damage fraction where the damage fraction is a time in minutes of an actual load time divided by a total time to failure, where the total time to failure may be calculated as a resultant from a function, where the function is a stress to failure in unit time divided by the average ignition stress yielding a quotient, the quotient being raised to the power of a damage exponent, the exponentially raised quotient being multiplied by a temperature shift factor; adding the current damage fraction to the previous cumulative damage to determine the current total of the cumulative damage; and repeating the steps until all time prior to ignition and through the entire time interval of ignition pressure transient up to steady state motor operating pressure has been included.

In equation 1, the grain stress arising from pressurization at any arbitrary motor age is calculated from the known stress at a reference age. In equation 2, the stress is adjusted for the conditioning temperature. In equation 3, the reference thermal contraction stress is adjusted for relaxation due to aging and lowering of the stress free temperature. In equation 4, the stress is adjusted for the conditioning temperature. The proportioned stress due to pressure generated at ignition by the combustion gases is added to the thermal stress, over small increments of time in equation 5, and the damage fraction is calculated in equation 6, where the fraction is the time at a particular load over the time to failure. The fractions are added to get the cumulative damage.

In the example that follows, the method will be demonstrated by analysis of pressurization loading in a solid propellant rocket motor whose load history is otherwise dominated by thermal contraction of the solid propellant bonded within a steel pressure vessel. A concern are stresses within the solid propellant itself, where the propellant, or grain, is usually bonded within its pressure vessel, often made of steel. Pressurization stresses are produced when the combustion gases fill the vessel, causing the case and grain to expand outward. As previously noted, thermal grain stress arising from thermal contraction is produced when the case and grain system is cooled and propellant, having coefficient of thermal expansion roughly ten times that of steel, cannot shrink unencumbered.

Initially, as shown in Table I of FIG. 2, the thermal grain bore stress $\sigma_T$ is about 49.8 lbs/in² when the conditioning temperature is 45° F., 43.7 lbs/in² when the conditioning temperature is 55° F., and 32.6 lbs/in² when the conditioning temperature is 77° F. After four years of ambient aging, when the motor is conditioned to these temperatures, the grain bore stress $\sigma_T$ has dropped from 43.7→29.3, from 32.6→23.5 and from 32.6→12.1 respectively. The propellant grain mass has relaxed, and it does not change much after four years until the propellant has aged 15 years, after which time the grain bore stress $\sigma_T$ starts to increase 28.6→29.3, 22.3→22.8, and 9.7→10.0. This stress increase occurs once the Stress Free temperature $T_{SF}$ has stabilized at 95° F. The ratio of the relaxation modulus $E_R$ (lbs/in²) at some motor age to its initial value, before any aging has occurred, $E_{Ro}$ is shown to continue to increase without the deflection observed for the grain bore stress $\sigma_T$ after 15 years. The reader is reminded that $E_R$ is the force per area ($\sigma_T$) divided by the strain $\epsilon$, where strain is the change in length (inches) divided by the length (inches)).

After 20 years, the thermal grain bore stress $\sigma_T$ still remains, and this stress continues to result in increased fatigue, which is quantified in terms of damage, where damage is a fraction. The damage fraction is cumulative, and the total possible damage is 1 (or 100%). When the damage is 1, the rocket motor propellant grain will fracture, e.g. crack. The impact of such a fracture on motor operation is highly variable ranging from negligible through catastrophic destruction prior to the completion of the mission. The impact depends on the size of the fracture, its location and the particular grain design.

In addition to thermal contraction stresses, pressurization stresses are produced on ignition when combustion gases cause the case and grain to expand. The pressure causes ignition fatigue in the propellant. Proportionality is used to adjust the reference finite element model results so they may be applied to a combination of motor age and grain conditioning temperature at ignition, and be combined with the thermal contraction stresses, and other similarly proportioned stresses to determine the total damage fraction and the cumulative damage fraction.

To adjust the reference finite element grain stress that arises from pressurization, the impact of changes in propellant stiffness over time is considered, and the effect of the motor conditioning temperature is included.

Equation (1) is used to estimate grain stress $\sigma_{p,age}$ arising from pressurization at a given pressure, for a motor of any age;

$$\sigma_{p,age} = \sigma_{p,ref} E_{tan}/E_{tan,ref} \qquad (1)$$

where $\sigma_{p,ref}$ is the reference component of grain stress that arises from pressurization, calculated by finite element analysis for a motor of reference age (9 years in this example). The quantity $\sigma_{p,age}$ is the pressure component of grain stress in a motor of the age of interest. The conversion between the reference and desired age is calculated by multiplying by a propellant modulus ratio, where $E_{tan}$ is the constant strain rate tangent modulus from the pressurization phase of a bi-rate uniaxial tensile test (i.e. a bi-rate test is one in which a propellant tensile coupon is first slowly elongated to the strain corresponding to that arising from thermal contraction of the grain at the conditioning temperature of ignition after which the test cell is pressurized to the level achieved during motor ignition and the coupon is pulled at the rapid rate corresponding to the ignition pressure rise rate). The ignition phase tangent modulus has been found to more faithfully represent ignition conditions than relaxation testing. The quantity $E_{tan,ref}$ is the tangent modulus of the reference age finite element analysis. The difference in these two moduli is attributed to propellant aging.

The reference finite element analysis will have been performed for a conditioning temperature of a specific motor. If a different temperature is of interest, a second step following application of equation (1) is required. To account for the effects of temperature on stresses arising from pressurization, equation (2) is used.

$$\sigma_{p,Temp} = \sigma_{p,age}(1 + \{T - T_{ref}\}\pi_K) E_R/E_{ref} \qquad (2)$$

T is the ignition conditioning temperature of interest, $T_{ref}$ is the temperature analyzed by the finite element analysis, $\pi_K$ is the temperature sensitivity to pressure, $E_R$ is the relaxation modulus for ignition at temperature T, and $E_{Rref}$ is the relaxation modulus for the temperature considered in the finite element analysis.

The bi-rate tangent modulus, the quantity used in equation (1), is generally not available for temperatures other than ambient. Therefore the relaxation modulus is substituted for the tangent modulus in equation (2). Relaxation moduli with superimposed pressures simulating ignition are also generally unavailable. The relaxation moduli of equation (2) may not, therefore, include the effect of pressure, i.e. they are data from ambient pressure tests, but do provide the desired temperature dependence.

Relaxation moduli are calculated using a time and temperature superposition method with a loading time in this case equal to the period needed for the motor to reach steady state operating pressure at the grain conditioning temperature of interest. Such a method is often represented by a relaxation master curve which provides the relationship between relaxation modulus, loading time, and temperature, (i.e. relaxation modulus versus $t_l/a_T$, where $t_l$ is the loading time and $a_T$ is the temperature shift factor) is discussed later.

Relaxation modulus is generally different for each combination of loading time and temperature owing to the viscoelastic nature of the propellant matrix material. The ignition loading time (interval from the first sign of propellant combustion to steady state operating pressure) may be adjusted to reflect its temperature dependence as well to correspond to the temperature, T, in equation (2). The superposition temperatures are, of course, the reference and value of interest to calculate $E_{Rref}$ and $E_R$, respectively.

Equation (2) results are only valid for motors having the same age as those motors that were used to compute $\sigma_{p,age}$ in equation (1). For every different motor age of interest a new value of $\sigma_{p,age}$ must be computed before applying equation (2).

Changes in relaxation modulus (for unpressurized propellant) and stress free temperature as the propellant ages will have an affect on thermal stress. To estimate the thermal stress with respect to age, at a common motor conditioning temperature equal to that used in the reference finite element analysis, equation (3) is used;

$$\sigma_{T,age} = \sigma_{T,ref}(E_R/E_{Rref})(\{T_{SF}-T_{ref}\}/\{T_{SF_{ref}}-T_{ref}\}) \qquad (3)$$

where $\sigma_{T,ref}$ is the reference component of grain stress that arises from grain thermal contraction, calculated by finite element analysis for a motor of reference age (9 years in this example). The quantity $T_{SF}$ is the grain stress free temperature at the age of interest, $T_{SF_{ref}}$ is the stress free temperature at the motor age represented by the finite element analysis, and $T_{ref}$ is the grain conditioned temperature analyzed with the finite element method. The quantity $E_R$ is the unpressurized relaxation modulus corresponding to propellant at the motor age of interest, and $E_{R_{ref}}$ is the corresponding value at the motor finite element analysis reference conditions.

The same time and temperature superposition method described earlier is employed to calculate relaxation modulus except now the loading time is the period needed for the grain to come to thermal equilibrium when the temperature of the ambient air surrounding the motor changes.

As previously discussed, the data in Table I illustrate the effect of the conditioning temperature on the bore stress. The higher the conditioning temperature, the lower the thermal grain bore stress. To estimate stress at different temperatures, for motors of a common age, equation (4) is used.

$$\sigma_{T_2} = \sigma_{T_1}(\{T_{SF}-T_2\}/\{T_{SF}-T_1\})(E_{R_2}/E_{R_1}) \qquad (4)$$

An example application of equation (4) is described below. In this example, the motor is 4 years old, and it has been conditioned at 45° F. ($T_1$). The predicted thermal grain bore stress $\sigma_{T_2}$ for propellant at another temperature ($T_2$), in this case, 55° F., is to be calculated. From Table I at 45° F. the stress free temperature $T_{SF}$ is 102° F., and the $\sigma_{T_1}$ is 29.3 lbs/in². We know from Table II in FIG. 3 (see col. 8, labeled $E_r$,lb/in²) that the relaxation modulus ratio of $E_{R_2}/E_{R_1}$ (i.e. 165/170) is 0.97; and from Table I that $\sigma_{T_1}$ is 29.3, ($T_{SF}$'$T_2$) is (102–55), which is 47, ($T_{SF}-T_1$) is (102–45) which is 57. Plugging the values into equation 1, $\sigma_{T_2}$=29.3*(47/57) *0.97=23.45, which rounds up to 23.5 lbs/in². as shown in Table I, col. 4.

All of the pressurization stresses of Table I correspond to steady state motor operation, i.e. they are the grain bore stress resulting from the maximum chamber pressure that is developed. A key concern when considering damage is the propellant's ability to resist cracking. In particular, as the pressure rises following ignition of the solid rocket motor, and as can be seen in Table I, the ignition pressurization grain bore stress $\sigma_p$ is sensitive to the ignition time, pressure and age. The ignition pressurization grain bore stress $\sigma_p$ and the thermal bore stress, $\sigma_T$, are additive. The units are lb/in². The determination of the damage therefore includes the fatigue damage after ignition, and continues to a point just before all of the bore propellant is consumed. If a crack were to open during ignition, i.e. the damage exceeds 1.0, then it could propagate ahead of the burning flame front causing the motor to produce too much thrust owing to the extra propellant surface area of the crack. If the crack is large enough, then the chamber pressure could even exceed the strength of the pressure vessel, leading to catastrophic failure.

To estimate the fatigue, which includes ignition damage, a pressurization stress history is constructed. Table III in FIG. 4 contains the results for ignition of a new motor that has been conditioned at 55° F. In this case, the ignition process spans 0.55 seconds, i.e., the interval required to go from zero chamber pressure to steady state operation in increments of 0.05 seconds. At zero time, the bore stress is purely thermal (i.e. no pressurization). To include the effect of the pressure component as pressurization proceeds the following relation equation (5) is used:

$$\sigma(t) = \frac{t}{t_{ign}}\sigma_p + \sigma_T \qquad (5)$$

Referring to equation (5) and Table III, $t_{ign}$ is the total ignition interval, in this case 0.55 seconds, and t is the instantaneous time (i.e. first column), $\sigma_T$ is the thermal stress, and $\sigma(t)$ is the grain circular bore surface stress, which is the average pressure stress over the time interval added to the total thermal stress. This simple interpolation formula is used to add, incrementally, in the steady state pressurization grain stress to the constant thermal contraction stress. An average stress over 0.05 second intervals is computed to facilitate the fatigue analysis.

An example calculation of equation (5) follows. At t=0, there is no pressurization, so $\sigma_p$=0, and $\sigma_T$=43.7 lb/in² (taken from Table I, age=0 years, conditioning temperature=55° F.). After 0.05 seconds, t=0.05 sec, $t_{ign}$=0.55 sec, $\sigma_p$=33.4 lb/in², and $\sigma_T$=43.7 lb/in². $\sigma$(0.05)=(0.05/0.55)*33.4+43.7=3.03+ 43.7=46.7. The $\sigma$ (0.05) (average) is (43.7+46.7)/2=45.2 lb/in². After one tenth of a second, $\sigma$(0.10)=(0.10/0.55) *33.4+43.7=7.07+43.7=49.8. The $\sigma$(0.10) (average) is (46.7+49.8)/2=48.2 lb/in².

The culmination of determining the average ignition stress about every five hundredths of a second for a duration of ignition time approximates integrating from zero to the duration of ignition time.

A damage fraction, D, is computed for each interval under the assumption that the stress remains constant within the interval using equation (6).

$$D \equiv \frac{t_l}{t_f} = \frac{t_l}{a_T\left(\frac{\sigma_0}{\sigma}\right)^B} \quad (6)$$

The damage fraction is a function of the time to failure $t_f$ and the actual load time $t_l$. The bore stress is $\sigma$. $\sigma_o$ is the stress that causes failure in unit time and B is the damage exponent. The derivation of B and $\sigma_o$ is described in greater detail later. The time to failure $t_f$ is a function of temperature as well as stress. The former dependence is captured in the temperature shift factor, $a_T$. The application of a superimposed pressure on the propellant has an impact on the fatigue damage parameters that must be accounted for in the computation of the damage fraction.

Computation of cumulative damage, using the results of Table III is illustrated in Tables IV and V. Note the Bore stress, $\sigma(t)$ is an average over the interval of time. These analyses represent alternate treatments of the dependence of fatigue parameters on the superimposed pressure. In all cases, the stress to cause failure in one minute has been used. Only damage through 0.55 seconds is shown, after which it is assumed that the grain bore surface has burned away. When applying equation (5) loading time is expressed in minutes.

In Table IV it is assumed that the quantities $\sigma_o$ and B assume their respective values when under superimposed pressure immediately upon application of the first increment of pressure, even though they were derived from coupons tested under pressures characteristic of motor steady state operation. In Table V $\sigma_o$ and B linearly vary from their respective values without superimposed pressure up to the values corresponding to motor steady state operation.

Table V may offer a more realistic model of the effect of superimposed pressure on fatigue properties. The cumulative damage at 0.55 second with the immediate and full change in $\sigma_o$ and B) is about half as much as what is calculated in Table IV, although both are relatively low (by definition fracture occurs when the cumulative damage reaches 1.0). Both approaches remain as viable options for the calculation of the damage.

The example of Tables III through V represent ignition of a new motor. Ignition of a rocket motor that has been deployed and shipped through a range of temperature environments is also a relevant case to consider. Therefore the cumulative effects of the pre-firing and firing loads must be considered.

To simplify the analysis of this complex sequence, an equivalent temperature history is sought to represent ignition. It will use fatigue parameters, i.e. $\sigma_o$ and B, in the absence of superimposed pressure so that it may be merged seamlessly with the analysis of the complex temperature history of the prefiring logistic environment. This latter sequence consists solely of grain loading arising from thermal contraction of the propellant.

Table VI has a step cooling history that has been constructed to yield about the same damage at 48 days as the motor ignition loading of Tables IV and V. Table VI has employed values of $\sigma_o$ and B that reflect the fatigue process without the presence of superimposed pressure. However, in an actual analysis, this history follows the logistic temperature history to estimate the total fatigue damage of a motor deployed for some period and expended. The temperatures are selected to be quite low to exacerbate the thermal contraction stress. At −67.9° F., the bore stress in this model is 66.7 lbs/in².

Figure 8:
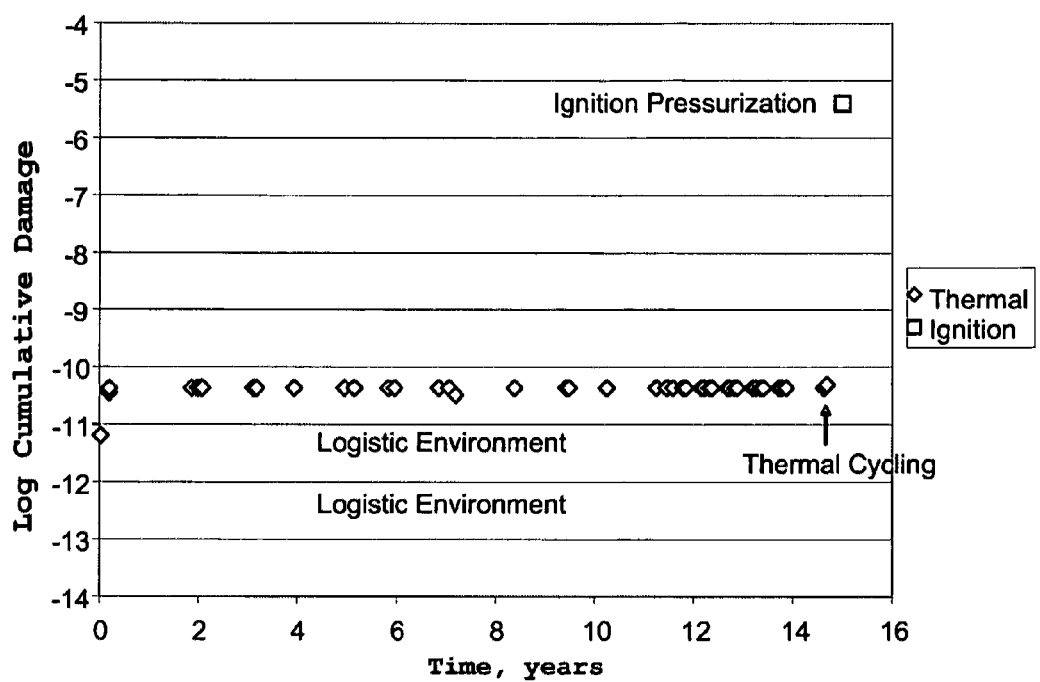
FIG. 8 is a semilogarithmic graph of a complex thermal sequence followed by motor ignition.

In FIG. 8 is a semilogarithmic graph of a rocket having a complex thermal sequence spanning fifteen years followed by motor ignition. The thermal environment consists of a logistic environment deployment, then a life sequence intended to mimic the seasonal temperature variation, followed by temperature cycling to −20° F., and then motor ignition. It can be clearly seen that the motor ignition event produces the most damage, unambiguously identifying it as the dominant load. The log of the cumulative damage fraction prior to ignition is about −10.3, and after ignition −5.3, which is an increase of about 100,000. The percent cumulative damage fraction after ignition is (100*0.0000050) about 0.000050.0%. One can conclude that even though there was a large increase in the cumulative damage fraction, the damage is still far from 1.

To summarize, a method for forecasting fatigue damage of a solid rocket motor through ignition utilizing a proportionality principle has been proposed to estimate pressurization and thermal stresses in a rocket motor for a combination of conditioning temperature, propellant age, and grain stress free temperature. The result is used to estimate ignition pressurization cumulative damage for any combination of these three parameters. The results may be compared with prior thermal contraction loads to determine the dominant load in the cumulative damage.

Furthermore, from Table VI, the step cooling using modeling based on stress arising from thermal contraction can be used to represent ignition pressurization damage because a temperature sequence can be found that produces the same magnitude of cumulative damage.

Figure 9:
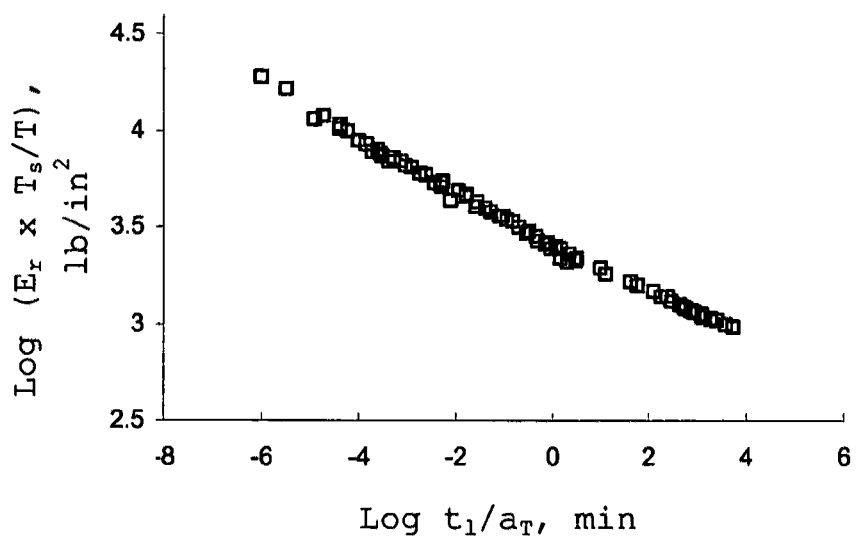
FIG. 9 is a graph of a solid propellant relaxation modulus, $E_r$, versus reduced time $t/a_T$ "master curve"

The calculations utilize the solid propellant Young's modulus, E, which depends on the temperature shift factor, $a_T$ and the load time, $t_l$. The relaxation modulus is a function of these two quantities. During a sustained load, such as would occur at a constant temperature dwell below the grain stress free temperature, the propellants filled rubbery matrix will undergo viscous flow such that the applied stress is gradually relieved. This relief is not total, however, because the polymeric matrix contains some density of three-dimensional polymeric cross-links that ultimately limit the degree of viscous flow. The relaxation modulus is an attempt to represent this complex behavior as a corresponding constant, or effective, Young's modulus. FIG. 9 is an example of a relaxation modulus master curve. The log graph in FIG. 9 illustrates the relationship of the solid propellant relaxation modulus, $E_r$, versus reduced time $t_l/a_T$. The graph allows a corresponding propellant modulus to be estimated for any combination of strain rate (load time) and temperature. The curve is derived by conducting individual relaxation (constant strain) tests at a number of different temperatures and "shifting" the individual curves, in time, to yield the master curve illustrated here. The quantity $T_s$ is a standard reference temperature, usually taken as 77° F. and T is the temperature of interest. When evaluating $E_r$, the absolute temperature (° K) is used.

The temperature shift factor $a_T$ depends on temperature via the WLF Equation (for Williams, Landel and Ferry) in equation (7), where $T_g$ is the material glass transition temperature and $C_1$ and $C_2$ are constants. For solid propellants $$\text{Log}_{10} a_T = \frac{-C_1(T - T_g)}{C_2 + (T - T_g)} \quad (7)$$

Figure 10:
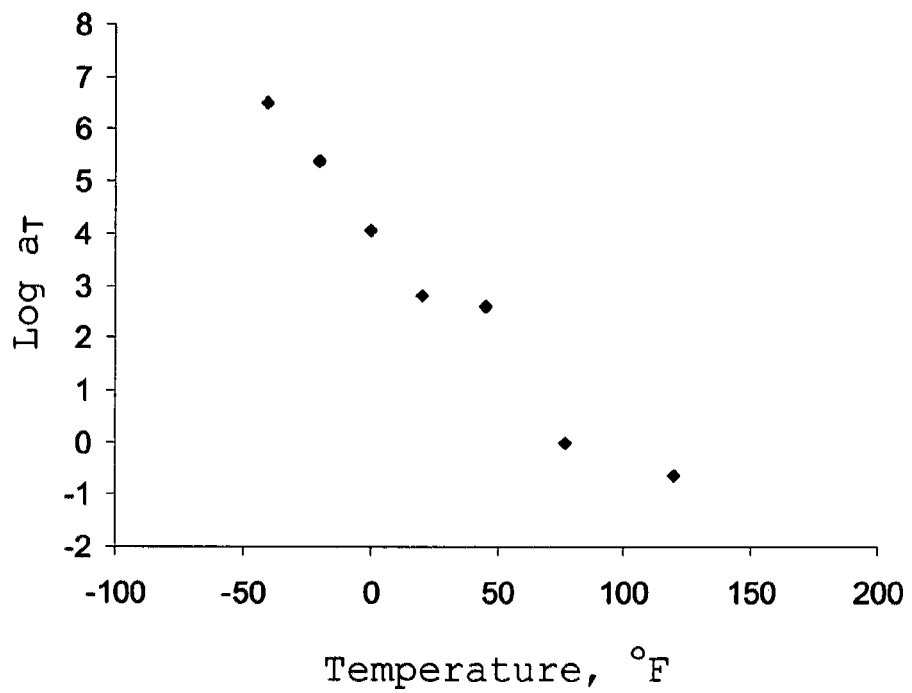
FIG. 10 is a graph that illustrates the solid propellant temperature shift factor versus temperature.

$C_1$ of around 17.4 and $C_2$ of around 51.6, adequately describe the temperature dependence for many materials but such may not always be the case with composite solid propellants. Individual temperature shift factor measurements, representing the propellant formulation of interest, are therefore often the best data available. $C_1$ and $C_2$ are generally the result of the data shifting process used to construct master curves such as FIG. 10 or from the construction of damage functions. Some common temperature shift factor data is illustrated in FIG. 10. Therefore, a convenient approach is to treat $C_1$, $C_2$ and $T_g$ as free parameters and use some curve fitting scheme, (e.g. the Levenberg-Marquardt), to determine the best fit to the input data. Alternately, a simple polynomial (usually second or third order) can be used. The propellant matrix glass transition temperature (Tg) generally ranges from −50° F. to −70° F. for polybutadiene rubbers. Cross-linking generally increases the (Tg). Some exemplary temperature shift factor data is illustrated in FIG. 10. It is derived through shifting relaxation modulus test data gathered at a variety of different temperatures (a single shift factor is obtained for each temperature in the test set). A reference temperature of 77° F. was used, corresponding to $a_T$=1.0.

Figure 11:
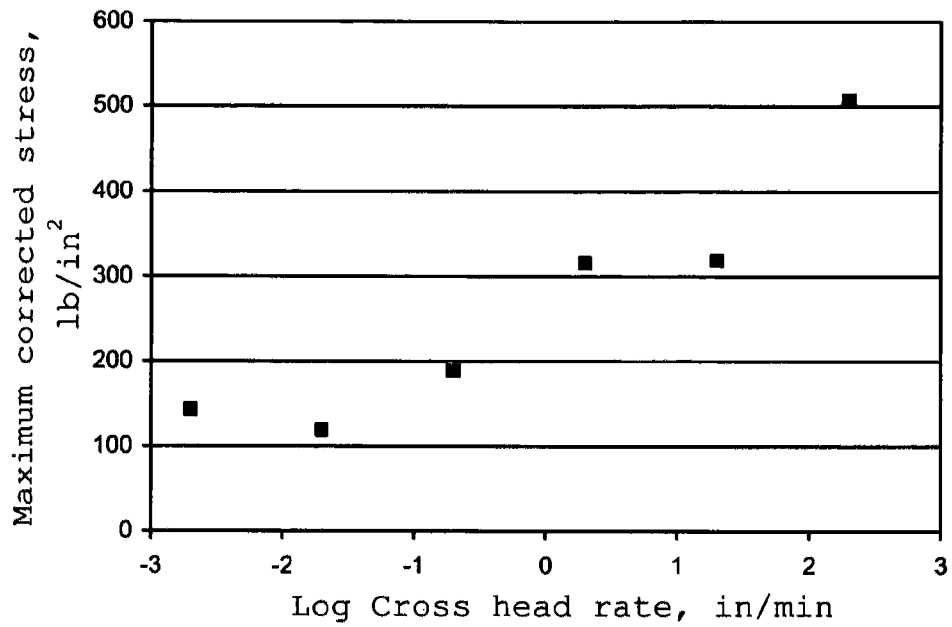
FIG. 11 is a graph that shows that for constant strain rate tensile data for a typical solid propellant that as the strain rate is increased the maximum corrected stress also increases. All specimens were conditioned at ambient temperature prior to testing. Each plotted point is the average of a number of tests.

The linear cumulative damage phenomenon may be quantified from laboratory tensile test data. Constant strain rate testing of propellant coupons to failure is the primary test employed. These are generally conducted across a wide spectrum of strain rates, e.g. 200 to 0.0002 inch/min, to obtain a large distribution of applied stress and time to failure. This result is assured owing to the visco-elastic nature of the propellants rubber matrix, i.e. the higher strain rates afford less time for the viscous flow that tends to relieve stress. The result is a significant increase in the maximum stress, observed in a constant strain rate test, as the strain rate is raised. FIG. 11 illustrates the dependence of maximum stress achieved in a constant strain rate test on the strain rate. The higher strain rates correspond to shorter times to failure.

Figure 12:
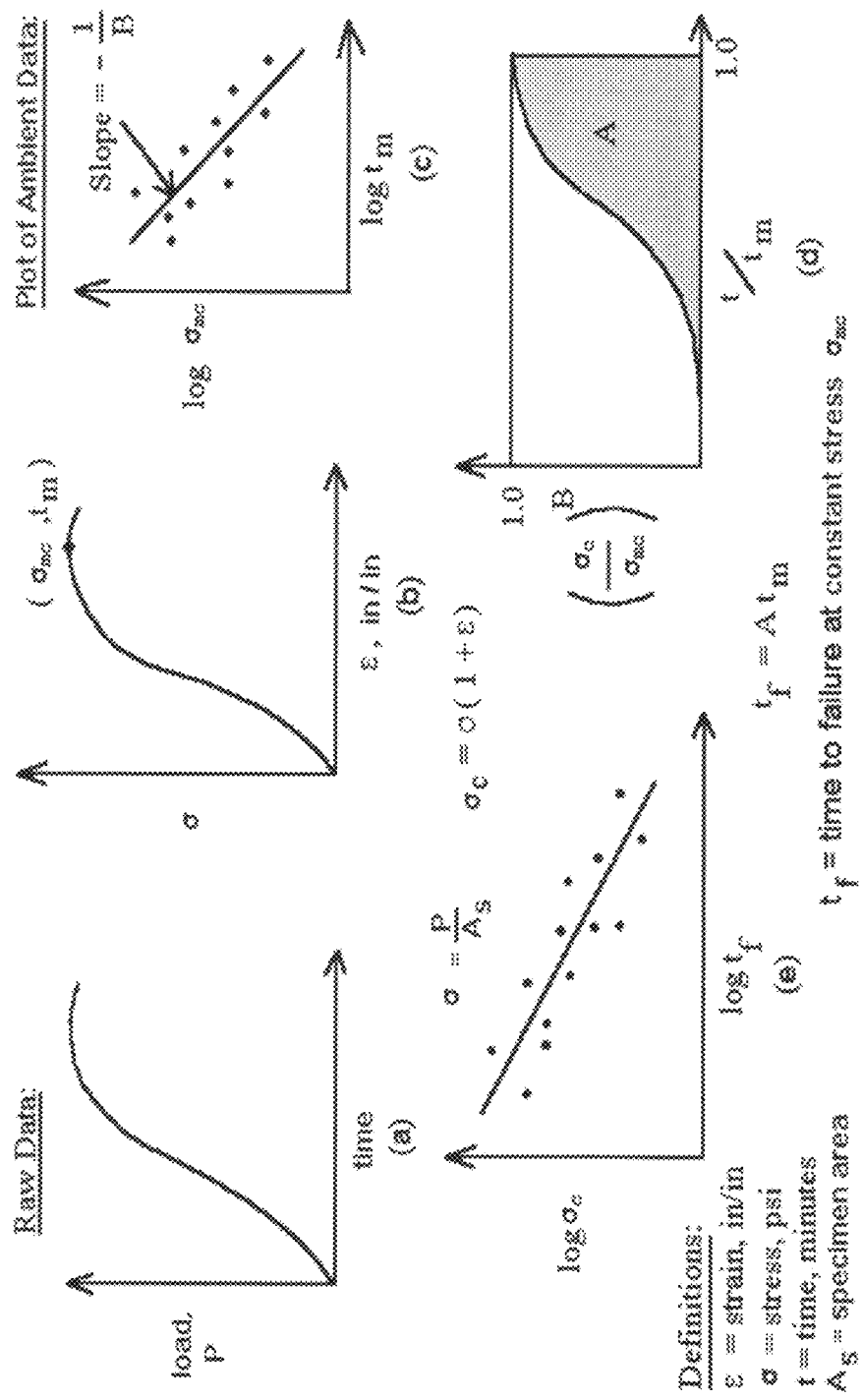
FIG. 12 is a series of graphs that illustrate a sequence of steps used to reduce the data for a cumulative damage analysis.

The sequence of steps used to reduce the data for a cumulative damage analysis is illustrated in FIG. 12. The raw load versus time data (FIG. 12a) are first converted to corrected, or true stress, versus strain (FIG. 12b). Corrected stress is calculated using the instantaneous value of the specimens cross section as it necks down during the course of the test. A logarithmic plot of each tests' maximum corrected stress versus the time required to reach it is made, using only the data collected from tests conducted at a standard reference temperature, usually ambient (FIG. 12c). The negative reciprocal of the slope of this curve is an initial estimate of the damage exponent, B. A normalized stress versus strain plot is constructed for each tensile test with the exponent in hand, including those performed at temperatures other than ambient (FIG. 12d). The area under these curves, from the start of the test to the point where maximum corrected stress is reached, is multiplied by the time to reach maximum corrected stress. The result is the time in which failure would have occurred had the test been conducted at a constant stress, equal to the maximum corrected value. A damage function may now be derived that consists of a logarithmic plot of maximum corrected stress versus the just computed time to failure (FIG. 12e).

Data representing each temperature will form a continuous curve (not shown in FIG. 12). The ambient data are taken as the reference curve and all of the other data are combined with it using a shifting procedure. This approach is simply a method of adding (or subtracting) a constant to the time to failure for each data set corresponding to a given temperature so that it overlaps the ambient temperature data curve. These constants are in fact the shift factors, $a_T$. Once the shifting process is completed for all of the data another linear regression fit is made of the damage function curve. The negative reciprocal of the slope of this curve is the final estimate of B. This exponent is the damage exponent that appears in equation (6). The quantity $\sigma_o$ is the intercept of this curve, i.e. the value of stress at log $t/a_T$=0 and is referred to as the stress that causes failure in unit time.

It is to be understood that the foregoing description and specific embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A method for forecasting fatigue damage of a solid rocket motor through ignition, comprising:
    dissecting a solid propellant rocket motor to obtain grain sections;
    machining tensile coupons from the grain sections where the tensile coupons are oriented in a direction of maximum stress;
    performing constant strain rate to failure uni-axial tensile tests with propellant coupons,
        wherein said tests are performed at ambient atmospheric pressure for analysis of motor pre-ignition loading and with superimposed pressure for analysis of rocket motor ignition;
    reducing constant strain rate propellant tensile data to a form that represents constant stress and obtaining a relationship between constant stress and time to failure;
    obtaining separate relationships for both atmospheric and superimposed motor ignition pressures;
    performing relaxation modulus testing of propellant coupons;
    reducing relaxation modulus test results to obtain a master curve of modulus versus reduced time, i.e. $t/a_T$, where t is loading time and $a_T$ is the temperature shift factor;
    performing bi-rate uni-axial testing of propellant tensile coupons where the first phase test stage simulates slow straining to pre-motor ignition grain thermal contraction strain and the second stage consists of rapid straining with superimposed pressure to simulate motor ignition, wherein maximum tangent modulus is measured from stage two and is used to estimate grain ignition stress;
    performing long term constant strain testing of solid propellant tensile coupons and measuring permanent set over time;
    reducing observations of permanent set to obtain solid propellant grain stress free temperature over time;
    accelerating testing of solid propellant grain sections where samples of material are placed in high temperature ovens, each maintained at a different temperature;
    repeating constant strain rate, relaxation modulus, permanent set, and bi-rate tensile tests upon periodic withdrawal of material from the acceleration temperatures;

fitting data to an Arrhenius model for determine the rates at which the individual properties change over time at ambient temperature,
  wherein said rates are used to estimate physical and mechanical properties to calculate fatigue damage for ignition of a rocket motor of any arbitrary age of interest;
  building a finite element analysis reference that comprises a grain stress from pressurization, a relaxation modulus, a tangent modulus, a conditioning temperature, a thermal stress from contraction after manufacture, and a stress free temperature;
adjusting an ignition pressure grain stress at ignition to account for any changes in propellant stiffness from the reference grain stress as indicated by a change from the reference tangent modulus;
adjusting the ignition pressure grain stress to account for a difference in an ignition conditioning temperature and the reference conditioning temperature, and a difference in an ignition relaxation modulus and the reference relaxation modulus;
adjusting the ignition pressure grain stress to account for a temperature sensitivity to pressure;
adjusting a thermal grain stress over an interval of time to account for a difference in a stress free temperature at an age and the reference stress free temperature, and a difference in a relaxation modulus at an age and the reference relaxation modulus;
adjusting the thermal grain stress to account for a difference in a second conditioning temperature and the stress free temperature, and a first conditioning temperature and the stress free temperature, and a ratio of the relaxation moduli at the second temperature divided by the relaxation moduli at the first temperature;
determining an ignition stress over a short time interval by adding the thermal grain stress to the ignition pressure grain stress, where the ignition pressure grain stress is a fraction of an instantaneous time divided by a total time for the ignition;
determining an average ignition stress by taking the average of the ignition stress at the current time interval and the ignition stress at the previous time interval;
determining a damage fraction, where the damage fraction is an actual load time divided by a total time to failure, wherein the total time to failure can be calculated as a resultant from a function,
  wherein said function is a stress to failure in unit time divided by the average ignition stress yielding a quotient, said quotient being raised to the power of a damage exponent, said exponentially raised quotient being multiplied by a temperature shift factor.

2. The method according to claim 1, wherein said damage fraction is alternately expressed as a decimal quotient of the time in minutes of an actual load time divided by the resultant time after which failure occurs at that magnitude of load.

3. The method according to claim 2, wherein said damage fraction is cumulative to cover all the time intervals during ignition and any time from a day of manufacture through ignition.

4. The method according to claim 3, wherein said damage fraction prior to ignition is substantially attributable to thermal stress generated by thermal contraction of the propellant.

5. The method according to claim 1, wherein said damage exponent is a negative reciprocal of the slope of the log of the stress in force per area (pounds per square inch) versus the log of the time in minutes.

6. The method according to claim 3, wherein said cumulative damage is quantified from laboratory tensile test data, and wherein constant strain rate testing of propellant coupons to failure is employed.

7. The method according to claim 1, wherein the temperature shift factor is determined for a propellant formulation of interest so that best data available are the result of the data shifting method used to construct master curves.

8. The method according to claim 1, wherein the temperature shift factor is derived by conducting individual relaxation constant strain tests at a number of different temperatures and the individual curves are shifted in time to yield the master curve.

9. The method according to claim 1, wherein the pressure is treated as a constant pressure, where the constant pressure is a superimposed pressure derived from laboratory testing.

10. The method according to claim 1, wherein the pressure exists only after ignition, and increases until it reaches a constant value.

11. The method according to claim 1, wherein a step cooling history indicates that thermal contraction at temperatures on the order of about −30 to about −70° F. yields about the same damage as motor ignition loading.

12. A method for forecasting fatigue damage of a solid rocket motor through ignition, comprising:
  adjusting an ignition pressure grain stress at ignition to account for any changes in propellant stiffness from a reference grain stress as indicated by a change from a reference tangent modulus;
  adjusting the ignition pressure grain stress to account for a difference in an ignition conditioning temperature and a reference conditioning temperature, and a difference in an ignition relaxation modulus and a reference relaxation modulus;
  adjusting the ignition pressure grain stress to account for a temperature sensitivity to pressure;
  adjusting a thermal grain stress over an interval of time to account for a difference in a stress free temperature at an age and a reference stress free temperature, and a difference in a relaxation modulus at an age and a reference relaxation modulus;
  adjusting the thermal grain stress to account for a difference in a second conditioning temperature and a second stress free temperature, and a first conditioning temperature and a first stress free temperature, and a ratio of relaxation moduli at the second temperature divided by the relaxation moduli at the first temperature;
  determining an ignition stress over a short time interval by adding the thermal grain stress to the ignition pressure grain stress, where the ignition pressure grain stress is a fraction of an instantaneous time divided by a total time for the ignition;
  determining an average ignition stress by taking the average of the ignition stress at the current time interval and the ignition stress at the previous time interval; and
  determining a damage fraction, where the damage fraction is a time in minutes of an actual load time divided by a total time to failure,
    wherein the total time to failure is calculated as a resultant from a function,
    wherein said function is a stress to failure in unit time divided by the average ignition stress yields a quotient,
    wherein said quotient is raised to the power of a damage exponent, and
    wherein said exponentially raised quotient is multiplied by a temperature shift factor.

13. The method according to claim 12, wherein said damage fraction is cumulative to cover all time intervals during ignition and any time from a day of manufacture through ignition.

14. The method according to claim 12, wherein said damage fraction prior to ignition is substantially attributable to thermal stress generated by thermal contraction of the propellant.

15. The method according to claim 13, wherein said cumulative damage after ignition is compared with the cumulative damage prior to ignition to determine a loading event that causes produces the greatest damage.

16. The method according to claim 13, wherein said average ignition stress is a bore stress of a pressure chamber of the rocket, and the bore stress is a point of highest stress.

17. The method according to claim 12, wherein said short time interval is on the order of about five hundredths of a second.

18. The method according to claim 17, wherein the culmination of determining the average ignition stress about every five hundredths of a second for a duration of ignition time approximates integrating from zero to the duration of ignition time.

19. A method for forecasting fatigue damage of a solid rocket motor through ignition, comprising:
   adjusting an ignition pressure grain stress at ignition to account for any changes in propellant stiffness from a reference grain stress as indicated by a change from a reference tangent modulus;
   adjusting the ignition pressure grain stress to account for a difference in an ignition conditioning temperature and a reference conditioning temperature, and a difference in an ignition relaxation modulus and a reference relaxation modulus;
   adjusting the ignition pressure grain stress to account for a temperature sensitivity to pressure;
   adjusting a thermal grain stress over an interval of time to account for a difference in a stress free temperature at an age and a reference stress free temperature, and a difference in a relaxation modulus at an age and a reference relaxation modulus;
   adjusting the thermal grain stress to account for a difference in a second conditioning temperature and a stress free temperature, and a first conditioning temperature and a stress free temperature, and a ratio of relaxation moduli at the second conditioning temperature divided by the relaxation moduli at the first conditioning temperature;
   determining an ignition stress over a short time interval by adding the thermal grain stress to the ignition pressure grain stress, where the ignition pressure grain stress is a fraction of an instantaneous time divided by a total time for the ignition;
   determining an average ignition stress by taking the average of the ignition stress at the current time interval and the ignition stress at the previous time interval;
   determining a damage fraction, where the damage fraction is a time in minutes of an actual load time divided by a total time to failure,
      wherein the total time to failure can be calculated as a resultant from a function,
      wherein said function is a stress to failure in unit time divided by the average ignition stress yields a quotient,
      wherein said quotient is raised to the power of a damage exponent, and
      wherein said exponentially raised quotient is multiplied by a temperature shift factor;
   adding the current damage fraction to the previous cumulative damage for determining the current total of the cumulative damage; and
   repeating the steps until all time prior to ignition and upon reaching motor operating pressure, after ignition, has been included.

20. The method according to claim 19, wherein said short time interval is about five hundredths of a second.

* * * * *